(12) United States Patent
Aslam (10) Patent No.: US 12,303,214 B2
(45) Date of Patent: May 20, 2025

(54) NEEDLE GUIDE DEVICES AND RELATED METHODS

(71) Applicant: Mayo Foundation for Medical Education and Research, Rochester, MN (US)

(72) Inventor: Nabeel Aslam, Ponte Vedra Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 77 days.

(21) Appl. No.: 18/386,847

(22) Filed: Nov. 3, 2023

(65) Prior Publication Data

US 2024/0148443 A1 May 9, 2024

Related U.S. Application Data

(60) Provisional application No. 63/422,749, filed on Nov. 4, 2022.

(51) Int. Cl.
*A61B 5/00* (2006.01)
*A61B 17/34* (2006.01)
(Continued)

(52) U.S. Cl.
CPC .......... *A61B 34/20* (2016.02); *A61B 17/3403* (2013.01); *A61M 5/427* (2013.01); *A61B 2034/2055* (2016.02)

(58) Field of Classification Search
CPC ............................ A61B 17/3403; A61M 5/427
See application file for complete search history.

(56) References Cited

U.S. PATENT DOCUMENTS

| 4,489,730 A | * | 12/1984 | Jingu | A61B 17/3403 601/2 |
| 5,052,396 A | * | 10/1991 | Wedel | A61B 8/4422 604/116 |
| 10,244,944 B2 | | 4/2019 | Mullani | |

OTHER PUBLICATIONS ameriburn.org [online], "Scald Injury Prevention Educator's Guide," available on or before Feb. 14, 2020, via Internet Archive: Wayback Machine URL <https://web.archive.org/web/20200214161743/http://ameriburn.org/wp-content/uploads/2017/04/scaldinjuryeducatorsguide.pdf>, retrieved on Oct. 30, 2024, retrieved from URL<http://ameriburn.org/wp-content/uploads/2017/04/scaldinjuryeducatorsguide.pdf>, 20 pages.

(Continued)

*Primary Examiner* — Rajeev P Siripurapu
(74) *Attorney, Agent, or Firm* — Fish & Richardson P.C.

(57) ABSTRACT

A trans-illuminating needle guide device for guiding a needle into and illuminating an arteriovenous (AV) fistula in a subject includes: a housing comprising a base, a needle guide insert having a pair of opposing side walls defining a first angled slot, a second angled slot, and a plurality of grooves, a needle guide having a guide channel configured to receive the needle, a first deflectable plate configured to be received by the first angled slot and the plurality of grooves, and a second deflectable plate configured to be received by the second angled slot, a first plurality of light emitting diodes (LEDs) disposed within the housing and configured to emit light of a first wavelength, and a second plurality of LEDs disposed within the housing and configured to emit light of a second wavelength, the second wavelength differing from the first wavelength.

17 Claims, 3 Drawing Sheets

(51) Int. Cl.
*A61B 34/20* (2016.01)
*A61M 5/42* (2006.01)

(56) References Cited

OTHER PUBLICATIONS

Barnett, "Tissue Cutting Mechanisms of Dyamic Needle Insertion," Thesis for the degree of Doctor of Philosophy, The Pennsylvania State University, College Of Engineering, May 2016, 140 pages.

bmecapstone.gatech.edu [online], "Adjustable Depth Guide for Hemodialysis Cannulation," upon information and belief, available no later than Jun. 24, 2022, retrieved on Oct. 16, 2024, retrieved from URL<https://bmecapstone.gatech.edu/s20-new-kidneys-on-the-block-mayo-and-baxter/>, 5 pages.

kffhealthnews.org [online], "Feds Pave The Way To Expand Home Dialysis—But Patients Hit Roadblocks," Aug. 2019, retrieved on Oct. 24, 2024, retrieved from URL<https://kffhealthnews.org/news/feds-pave-the-way-to-expand-home-dialysis-but-patients-hit-roadblocks/>, 6 pages.

Lee et al., "Standardized definitions for hemodialysis vascular access," Semin. Dial., Sep.-Oct. 2011, 24(5):515-524.

Lee et al., "Needle infiltration of arteriovenous fistulae in hemodialysis: risk factors and consequences," Am. J. Kidney Dis., Jun. 2006, 47(6):1020-1026.

Niyyar, "Ultrasound-based simulation for cannulation in outpatient hemodialysis units: An educational protocol," J. Vasc. Access, Jul. 2021, 22(4):585-589.

pharm.ucsf.edu [online], "The Kidney Project. Creating a bioartificial kidney as a permanent solution to kidney failure," upon information and belief, available no later than Nov. 4, 2022, retrieved on Oct. 24, 2024, retrieved from URL<https://pharm.ucsf.edu/kidney/need/statistics>, 3 pages.

Smith et al., "Thermal comfort of patients in hospital ward areas," J. Hyg., Feb. 1977, 78(1): 17-26.

Van Loon et al., "Cannulation and vascular access-related complications in hemodialysis: factors determining successful cannulation," Hemodial. Int., Oct. 2009, 13(4):498-504.

Walker et al., "Home hemodialysis: a comprehensive review of patient-centered and economic considerations," Clinicoecon. Outcomes Res., Feb. 2017, 9:149-161.

* cited by examiner

NEEDLE GUIDE DEVICES AND RELATED METHODS

CROSS-REFERENCE TO RELATED APPLICATIONS

This application claims the benefit of U.S. Patent Application Ser. No. 63/422,749, filed on Nov. 4, 2022. The disclosure of the prior application is considered part of (and is incorporated by reference in) the disclosure of this application.

TECHNICAL FIELD

This disclosure describes needle guide devices and related methods of guiding a needle to and locating a blood vessel of a subject in need thereof.

BACKGROUND

As a person's kidney fails, kidney function can be supplemented through the process of hemodialysis. Hemodialysis requires access to the patient's blood, which is typically done by cannulating either the arteriovenous (AV) fistula or AV graft in the patient's arm, or a catheter in the patient's neck vein. An AV fistula or AV graft is an access created when a surgeon connects a vein and artery to provide increased blood flow and create a stronger vessel, which can survive repeated damage from the cannulation process. An AV graft performs the same function through use of an artificial tube connecting a vein and artery. The major risk to patient health regarding the cannulation process is infiltration, which occurs when the cannulation needle is inserted incorrectly and causes bleeding under the patient's skin. A minor infiltration occurs when the needle grazes the vein, causing an easily treatable leakage. In contrast, a major infiltration occurs when the needle punctures completely through the access, thereby creating two openings and risking potential vessel collapse, missed treatments, catheter dependence, and even death if not treated properly. As such, there is a clear need for a solution that aids in the hemodialysis process to reduce the risk of major infiltrations.

SUMMARY

In general, this disclosure describes needle guide devices and related methods. Such needle guide devices can be used for performing cannulating and/or location a blood vessel of a patient (e.g., an AV fistula or AV graft) for a dialysis treatment.

In one aspect, this disclosure is directed to a trans-illuminating needle guide device for guiding a needle into and illuminating an arteriovenous (AV) fistula in a subject, including: a housing comprising a base; a needle guide insert having a pair of opposing side walls defining a first angled slot, a second angled slot, and a plurality of grooves, the needle guide insert configured to be removably coupled to the base; a needle guide having a guide channel configured to receive the needle, a first deflectable plate configured to be received by the first angled slot and the plurality of grooves, and a second deflectable plate configured to be received by the second angled slot; a first plurality of light emitting diodes (LEDs) disposed within the housing and configured to emit light of a first wavelength; and a second plurality of LEDs disposed within the housing and configured to emit light of a second wavelength, the second wavelength differing from the first wavelength, wherein each groove of the plurality of grooves corresponds to a different needle insertion depth, and wherein the first and second pluralities of LEDs are configured to illuminate the AV fistula or AV graft of the subject.

Embodiments may include one or more of the following features.

In some embodiments, the needle guide insert comprises a pair of deflectable tabs, each deflectable tab of the pair of deflectable tabs comprising a hook configured to engage a recess defined by the base.

In some embodiments, the channel is an open channel having a semi-cylindrical cross-section.

In some embodiments, the first deflectable plate comprises a pair of protrusions, each protrusion of the pair of protrusions extending from opposing edges of the first deflectable plate and configured to engage a groove from the plurality of grooves.

In some embodiments, each protrusion extends from the opposing edges in a direction that is perpendicular to a surface of the first deflectable plate.

In some embodiments, the first and second deflectable plates form a vertex and define an acute angle.

In some embodiments, the AV fistula or AV graft is: i) a superficial AV fistula or AV graft located at subcutaneous depth of less than about 4 millimeters (mm) from a skin surface, or ii) a deep AV fistula or AV graft located at subcutaneous depth of more than about 4 mm from a skin surface.

In some embodiments, the pair of opposing side walls define a track configured to engage a projection of a pair of opposing inner walls of the base.

In some embodiments, the pair of opposing side walls is parallel to and configured to abut the pair of opposing inner walls when the projection is engaged by the track.

In some embodiments, the projection and track extend longitudinally and are parallel to a bottom surface of the base.

In some embodiments, the first and second pluralities of LEDs are arranged in a U-shape.

In some embodiments, the first wavelength ranges from about 620 nanometers (nm) to about 700 nm.

In some embodiments, the second wavelength ranges from about 600 nm to about 615 nm.

In some embodiments, the LEDs are configured to emit light at an angle of dispersion of about 25 degrees.

In some embodiments, the needle insertion depth ranges from about 1 mm to about 8 mm.

In some embodiments, the needle guide insert is optically transparent or opaque.

In some embodiments, the angle of the needle is about 30 degrees to about 39 degrees.

Disclosed herein, in certain embodiments, are methods of guiding a needle into and illuminating an arteriovenous (AV) fistula in a subject, including: inserting a needle guide insert comprising a needle guide into a base of a housing of a trans-illuminating needle guide device; placing the trans-illuminating needle guide device on a skin surface of the subject; illuminating the skin surface and a subcutaneous tissue of the subject using a plurality of light emitting diodes (LEDs) disposed within the housing of the trans-illuminating needle guide device, thereby locating the AV fistula or AV graft within the subcutaneous tissue; selecting a needle insertion depth by adjusting the needle guide; inserting the needle into a guide channel of the needle guide to guide the needle; inserting the needle into the AV fistula or AV graft at the selected needle insertion depth; and disengaging the needle form the needle guide.

In some embodiments, selecting the needle insertion depth further comprises moving: i) a first deflectable plate of the needle guide along a second angled slot defined by a side wall of the needle guide insert, and ii) a second deflectable plate of the needle guide along a second angled slot and a groove of a plurality of grooves defined by the side wall of the needle guide insert.

In some embodiments, each groove of the plurality of grooves corresponds to a different needle insertion depth.

Some embodiments of the devices and methods described herein may provide one or more of the following advantages.

First, some embodiments described herein significantly decrease the rate of major infiltrations by implementing LED vein illumination technology and a mechanical depth guide alongside venous mapping. As previously mentioned, a major infiltration occurs when the needle punctures completely through the blood vessel (e.g., the AV fistula or AV graft) during insertion or a dialysis treatment, thereby creating two openings and risking potential vessel collapse, missed treatments, catheter dependence, and even death if not treated properly. Venous mapping, which can be conducted by a healthcare practitioner (e.g., a radiologist) after the maturation of the fistula, utilizes ultrasound to provide a clear image of the location and depth of the vessel below the surface of the skin. Thus, a user can select a desired needle insertion depth based on the venous mapping to ensure the blood vessel (e.g., the AV fistula or AV graft) is not punctured through.

Second, some embodiments described herein reduce uncertainty and variation in fistula location, stability, and depth to provide a more exact and consistent cannulation for each patient. The trans-illuminating needle guide device of the disclosure may be adjustable across a wide range of fistula depths and may illuminate the fistula while conserving the workflow by minimally interrupting the existing dialysis process.

Third, some embodiments described herein also accommodate complex anatomy and changes in fistula depth or location that occur naturally over time. For example, a user may detect changes in fistula depth or location after illuminating the AV fistula or AV graft using the light source of the trans-illuminating needle guide device.

Fourth, some embodiments described herein facilitate the cannulation process prior to a dialysis treatment because the device may be easily adopted in clinics without requiring unique training. The trans-illuminating needle guide device may be used in dialysis clinics by a healthcare practitioner (e.g., nurses and technicians) during cannulation. It can be used every time a patient is cannulated; however, it may be especially useful for new patients or new technicians where unfamiliarity exists between patient and provider. The trans-illuminating needle guide device may also be exceptionally useful for patients who are cannulated by a caregiver who has significantly less training than healthcare practitioner in clinics. By standardizing the cannulation process, the trans-illuminating needle guide device may make hemodialysis safer across a wide range of clinics and patients.

Fifth, some embodiments described herein facilitate flexible positioning of the trans-illuminating needle device (e.g., on a skin surface of the patient) such that the healthcare practitioner can operate from a medically advantageous location of the patient. The healthcare practitioner may thus position the trans-illuminating needle device on an area selected primarily based on the location of the AV fistula or AV graft.

Sixth, some embodiments described herein may help maintain sterility during the dialysis workflow (e.g., during cannulation). For example, the needle guide insert and/or the needle guide may be sterile, one-time use components to prevent patient infections caused by pathogen contamination of the trans-illuminating needle device. Furthermore, the housing of the trans-illuminating needle device can be amenable to be sterilized (e.g., by wiping the device using a disinfectant).

The use of the term "about," as used herein, refers to an amount that is near the stated amount by about 10% including increments therein. For example, "about" can mean a range including the particular value and ranging from 10% below that particular value and spanning to 10% above that particular value.

Unless otherwise defined, all technical and scientific terms used herein have the same meaning as commonly understood by one of ordinary skill in the art to which this disclosure pertains. Although methods and materials similar or equivalent to those described herein can be used to practice the various embodiments, suitable methods and materials are described herein. All publications, patent applications, patents, and other references mentioned herein are incorporated by reference in their entirety. In case of conflict, the present specification, including definitions, will control. In addition, the materials, methods and examples are illustrative only and not intended to be limiting.

The details of one or more embodiments of the disclosure are set forth in the accompanying drawings and the description below. Other features, objects, and advantages of the methods and devices described will be apparent from the description, the drawings, and the claims.

DESCRIPTION OF DRAWINGS

Like reference numbers represent corresponding parts throughout.

DETAILED DESCRIPTION

This document relates to devices and methods for guiding an insertion of a needle into a blood vessel. In some embodiments, the blood vessel is an AV fistula or AV graft or AV graft. In some embodiments, the devices and methods of the disclosure are used for guiding an insertion of a needle used to conduct a dialysis treatment. For example, this document provides devices and methods to locate and cannulate an AV fistula or AV graft or AV graft for a dialysis treatment.

Figure 1:
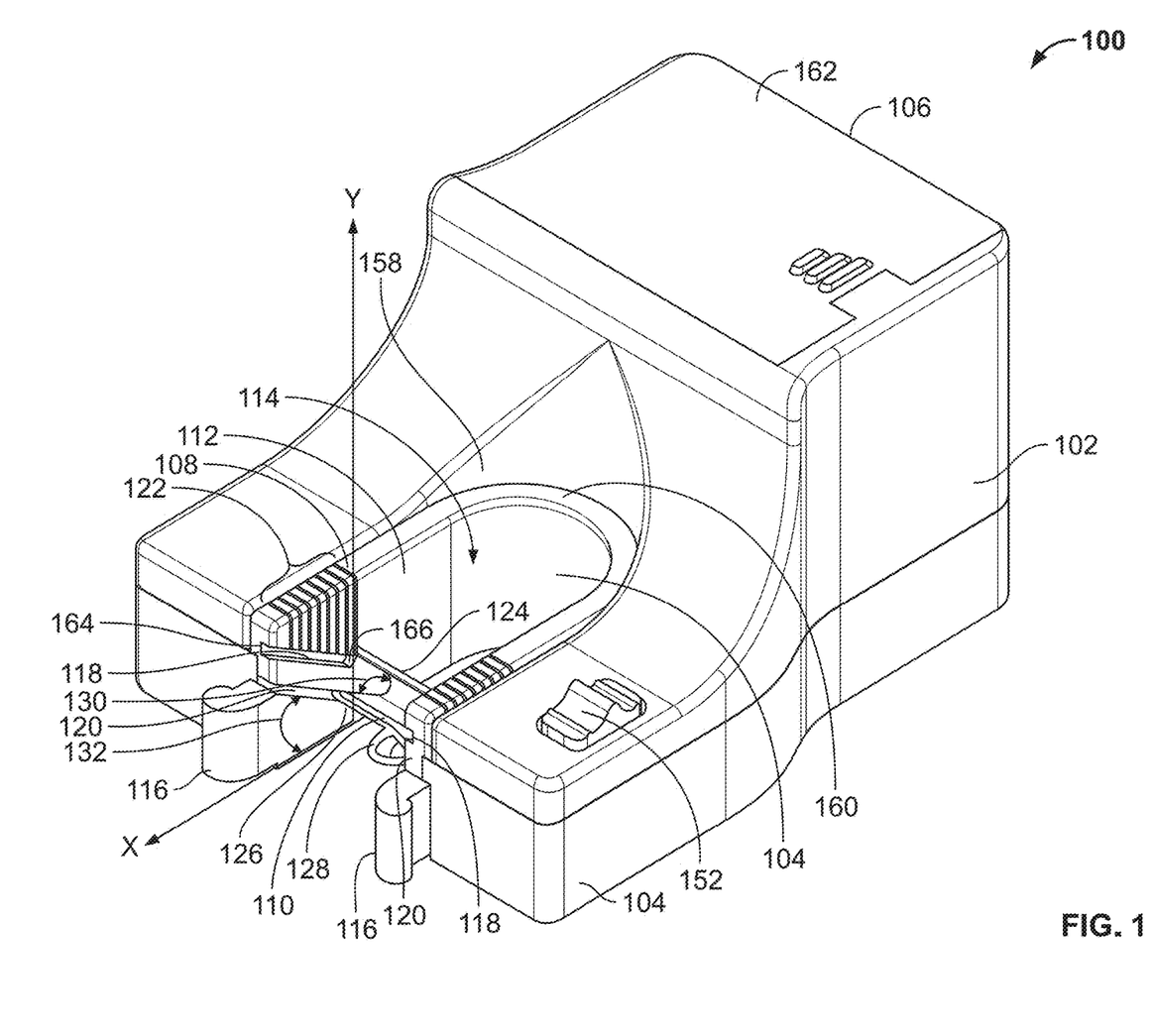
FIG. 1 is a perspective view of a trans-illuminating needle guide device.

FIG. 1 illustrates a trans-illuminating needle guide device 100 that is used to guide a needle into an AV fistula or AV graft or AV graft and illuminate the AV fistula or AV graft or AV graft in a subject (e.g., a patient). Example interventions that can be performed using the trans-illuminating needle guide device 100 include cannulation of a blood vessel (e.g., AV fistula or AV graft or AV graft) and/or localization of a blood vessel (e.g., AV fistula) for a dialysis treatment, for example. The trans-illuminating needle guide device 100 includes a housing 102, a needle guide insert 108, and a needle guide 110.

The housing 102 includes a base 104 having a U-shape that defines an opening 114. The base 104 is configured to be placed on a surface skin of a subject (e.g., a patient). The housing 102 includes a switch 152 configured to turn on and off a plurality of light sources of the trans-illuminating needle guide device 100. The housing 102 defines a compartment 106 configured to house one or more power sources. The compartment 106 is positioned distally from a vertex 160 formed by the opposing inner walls 158 of the base 104. The compartment 106 is rectangular in shape but may be any suitable shape. The compartment 106 is accessed through a compartment door 162 that is configured to be coupled with the housing 102. Example power sources include one or more electric batteries, such as rechargeable batteries and non-rechargeable batteries. Non-limiting examples of electric batteries include lithium batteries, alkaline batteries, carbon zinc batteries, silver oxide batteries, zinc air batteries, lithium ion batteries, and nickel cadmium batteries. The housing 102 is typically made of one or more materials that are relatively hard and/or that have a relatively low elasticity, such as, but not limited to, polypropylene, nylon, PTFE, ABS, polycarbonate, polystyrene, PEBA, and metals (e.g., aluminum, spring steel, or various soft metals).

Still referring to FIG. 1, the needle guide insert 108 is configured to be removably coupled to the base 104. Similarly to the base 104, the needle guide insert 108 has a U-shape formed by a pair of opposing side walls 112. Each side wall 112 defines a first angled slot 118 and a second angled slot 120. The first and second angled slots 118, 120 extend longitudinally from a proximal end 164 to a distal end 166 at an insertion angle 132 with respect to a horizontal axis (shown as the X-axis in FIG. 1) defined by a bottom surface of the trans-illuminating needle guide device 100. In some embodiments, the insertion angle 132 is about equivalent to the needle insertion angle at which the needle is inserted into a tissue of the subject. In some embodiments, the needle insertion angle ranges from about 30 degrees to about 39 degrees. In some embodiments, the needle insertion angle is at least about 30 degrees.

Each side wall 112 defines a plurality of grooves 122 extending above the first angled slot 118, along a vertical axis (shown as the Y-axis in FIG. 1) that is perpendicular to the bottom surface of the trans-illuminating needle guide device 100 and to the X-axis, as shown in FIG. 1. Each groove of the plurality of grooves 122 corresponds to a different needle insertion depth defined as the depth measured from a skin surface to a subcutaneous tissue of the subject. For example, the trans-illuminating needle guide device 100 includes eight grooves corresponding to a 1 millimeter (mm), 2 mm, 3 mm, 4 mm, 5 mm, 6 mm, 7 mm, and 8 mm depths. The plurality of grooves 122 are defined in increasing order of insertion depth with relation to the proximal end 164 to the distal end 166. That is, the groove 122 corresponding to the 1 mm needle insertion depth is the groove 122 that is closest to the proximal end 164 and farthest from the distal end 166. The groove 122 corresponding to the 8 mm needle insertion depth is the groove 122 that is closest to the distal end 166 and farthest from the proximal end 164.

Still referring to FIG. 1, the needle guide 110 includes a first deflectable plate 124, a second deflectable plate 126, and a guide channel 128. The first and second deflectable plates 124, 126 are integrally connected such that each deflectable plate is parallel to each other and together form a vertex defining an angle 130. Angle 130 can be an acute angle (i.e., angle 130 can be less than about 90 degrees). The first and second deflectable plates 124, 126 have a pair of opposing edges. Each edge of the first deflectable plate 124 is configured to be received by the first angled slot 118. Each edge of the second deflectable plate 126 is configured to be received by the second angled slot 120. The first deflectable plate 124 further includes a pair of protrusions. Each protrusion extends vertically, in a direction that is perpendicular to a surface of the first deflectable plate 124, from an opposing edge of the first deflectable plate 124 such that each protrusion is configured to engage a groove from the plurality of grooves 122. As such, a user can select a needle insertion depth by compressing the first and second deflectable plates 124, 126 to disengage the protrusion from a first groove, slide the first and second deflectable plates 124, 126 along the first and second angled slots 118, 120, and engage the protrusion with a second groove. In some embodiments, each protrusion extends horizontally, in a direction that is parallel to a surface of the first deflectable plate 124. The first and second deflectable plates 125, 126 are typically composed of a material that is rigid yet deflectable and able to be compressed. The first and second deflectable plates 125, 126 are able to sufficiently deform to facilitate engagement and disengagement of the protrusions with the plurality of grooves 122.

The guide channel 128 is integrally connected and extends from a bottom surface of the second deflectable plate 126. The guide channel 128 is an open channel having a semi-cylindrical cross-section. The guide channel 128 is configured to receive the needle to be guided and inserted into the subject. The guide channel 128 is configured to receive a variety of needle sizes including, but not limited to, 14 gauge needles, 15 gauge needles, 16 gauge needles, and 17 gauge needles.

Figure 2:
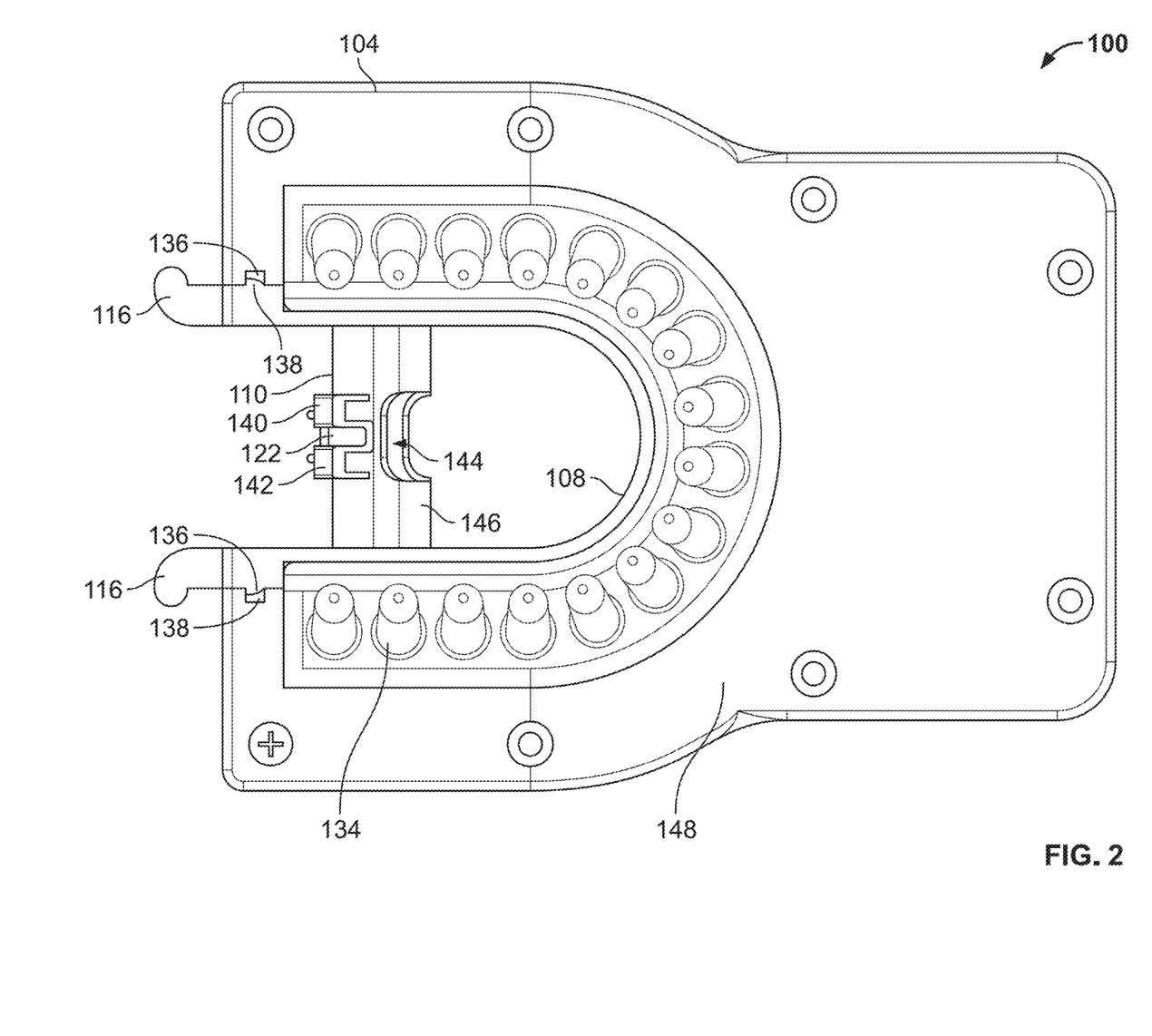
FIG. 2 is a bottom view of a trans-illuminating needle guide device.

Referring to FIG. 2, the trans-illuminating needle guide device 100 includes a plurality of light sources 134 (e.g., light emitting diodes (LEDs)) arranged in a U-shape and configured to illuminate a blood vessel (e.g., an AV fistula or AV graft or AV graft) of a subject. Each of the light sources 134 may be enclosed in a substantially opaque material such as a shell, which minimizes diffusion of light from the sides of the light source 134 (e.g., LEDs). The shell may be an opaque resin such as epoxy, an opaque elastomeric gasket, or other suitable opaque material. Each light source 134 is focused at a select angle to maximize the concentration of light at a select location within the tissue where a blood vessel (e.g., an AV fistula or AV graft or AV graft) is to be located. 1. The plurality of light sources 134 are configured to emit light at an angle of dispersion (or focus angle) of about 25 degrees. For example, each of the light sources 134 are placed at an angle (rather than flat) within the housing 102 to achieve an angle of dispersion (e.g., an angle of about 25 degrees). The relatively narrow focus angle may be beneficial as more light is directed into the tissue of the subject for trans-illumination. Each of the plurality of light sources 134 (e.g., LEDs) is disposed within the housing 102 on a bottom surface 148 of the trans-illuminating needle guide device 100. The plurality of light sources 134 (e.g., LEDs) is operatively coupled to the power source and switch 152. When in use, the switch 152 is depressed to turn on or off the plurality of light sources 134.

In some embodiments, the trans-illuminating needle guide device 100 includes a first plurality of LEDs and a second plurality of LEDs disposed within the housing 102 in a U-shape and configured to emit light of a first wavelength and a second wavelength, respectively. In some embodiments, the second wavelength differs from the first wavelength. The first plurality of LEDs can be configured to emit red light having a wavelength ranging from about 620 nm and 700 nm (e.g., about 620 nm to about 630 nm, about 620 nm to about 640 nm, about 620 nm to about 650 nm, about 620 nm to about 660 nm, about 620 nm to about 670 nm, about 620 nm to about 680 nm, about 620 nm to about 690 nm, about 630 nm to about 660 nm, about 630 nm to about 700 nm, or about 650 nm to about 700 nm). The second plurality of LEDs can be configured to emit orange light having a wavelength ranging from about 600 nm and 615 nm (e.g., about 600 nm to about 605 nm, about 605 nm to about 610 nm, about 610 nm to about 615 nm, or about 605 nm to about 615 nm). Given that light of the first and second wavelengths (e.g., red and yellow light) is absorbed by hemoglobin but substantially transmitted by other tissue, blood vessels under trans-illumination by light having these wavelengths appears black, while tissue that is not a blood vessel appears pink or red. Thus, light in the specified wavelength range provides maximum contrast between blood vessels and other subcutaneous tissue. Furthermore, the light of the first wavelength can advantageously be used to locate deep AV fistula or AV grafts or AV grafts located at a subcutaneous depth of more than about 4 mm (e.g., at a depth of about 4.1 mm to about 8 mm or more), while the light of the second wavelength can advantageously be used to locate superficial AV fistula or AV grafts or AV grafts located at a subcutaneous depth of less than about 4 mm (e.g., at a depth of about 1 to about 4 mm). As such, the user can easily use first and second pluralities of light sources of the trans-illuminating needle guide device 100 to locate and cannulate AV fistula or AV grafts or AV grafts at various depths.

Still referring to FIG. 2, the needle guide insert 108 includes a pair of opposing deflectable tabs 116 that are movable between an engaged position and a disengaged position. The pair of opposing deflectable tabs 116 are integrally connected to the side walls of the needle guide insert 108 and extend outwardly from a proximal face of the trans-illuminating needle guide device 100. Each deflectable tab 116 includes a hook 138 configured to engage a recess 136 defined by the base 104 when in the engaged position. The pair of deflectable tabs 116 are moved into their disengaged position when squeezed or compressed inwards (i.e., towards each other). In this embodiment, the needle guide insert 108 includes a pair of opposing deflectable tabs 116 are typically composed of plastic and are integrally formed. The material composition and dimensions of the pair of opposing deflectable tabs 116 are selected to allow a user to laterally displace the pair of hooks 138 relative to the recesses 136 with moderate force, and to allow the pair of opposing deflectable tabs 116 to return back to their original position when the force is released (i.e., the pair of opposing deflectable tabs 116 are resilient). In some embodiments, instead of being integrally formed, the pair of opposing deflectable tabs 116 can be separate components that are attached to the needle guide insert 108 by means known to one skilled in the art. Instead of being composed of plastic, the needle guide insert 108 and/or a pair of opposing deflectable tabs 116 can be made of a different material which has the aforementioned desired properties, for example, a resilient metal.

Still referring to FIG. 2, the needle guide 110 defines a hole 144 at the vertex 146. In some embodiments, the hole 144 provides the needle guide 110 a flexibility that allows the first and second deflectable plates of the needle guide 110 to be compressed. The needle guide 110 includes the guide channel 128 having a first arm 140 and a second arm 142 configured to partially enclose an elongate volume into which a portion of the needle is disposed when the needle is inserted into the guide channel 128. Cross-sectionally, the first and second arms 140, 142 are shaped to extend from a bottom surface of the second deflectable plate and not fully (e.g., partially) terminate toward each other, causing the guide channel 128 to have a semi-cylindrical body that is defined between the terminal ends of the first and second arms 140, 142. The opening of the semi-cylindrical body of the guide channel 128 runs the entire length of the guide channel 128 so as to define a slot through which a needle or other suitable elongate device can be easily inserted and/or removed from the guide channel 128 when desired. In some embodiments, at least the first and second arms 140, 142 are composed of a rigid material (e.g., a plastic) that enables the needle to be secured when inserted in the guide channel 128.

Figure 3:
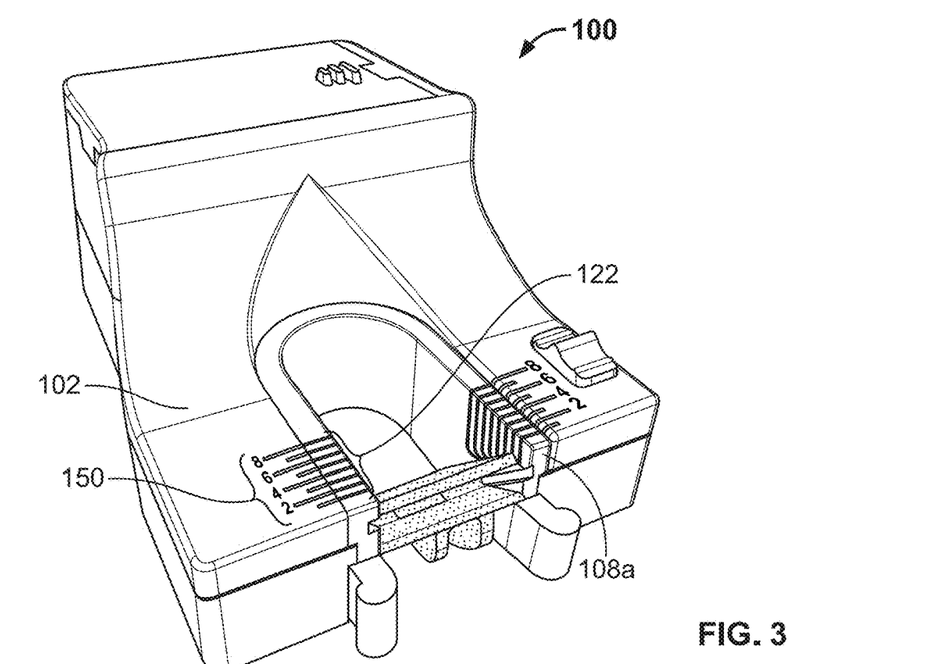
FIG. 3 is a perspective view of a trans-illuminating needle guide device including an opaque needle guide insert.
Figure 4:
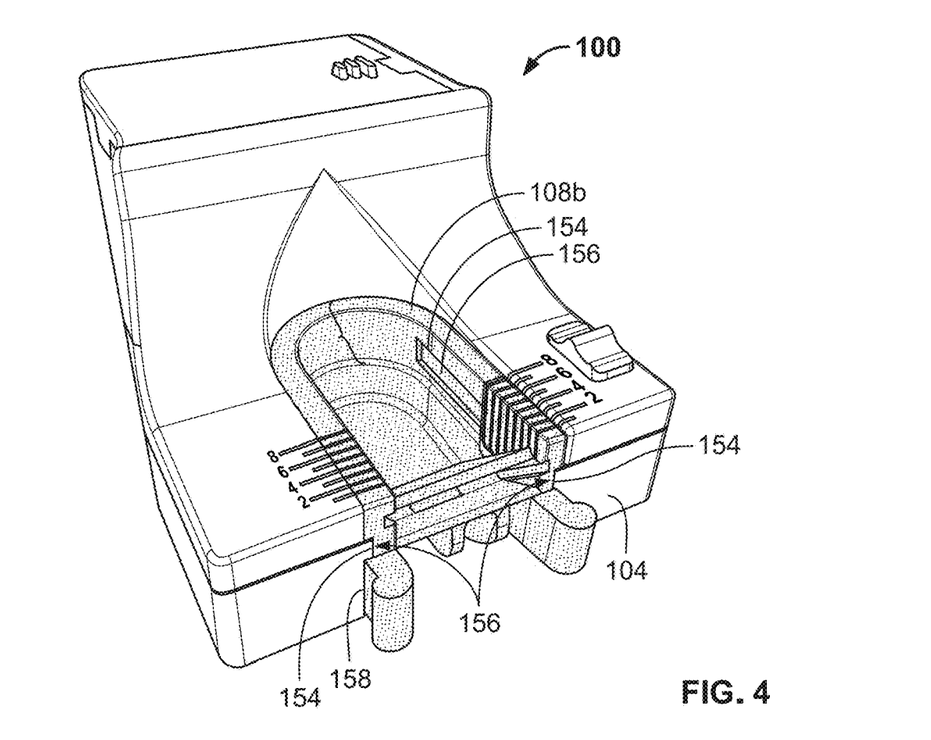
FIG. 4 is a perspective view of a trans-illuminating needle guide device including an optically transparent needle guide insert.

Referring to FIGS. 3 and 4, the trans-illuminating needle guide device 100 can include an opaque needle guide insert 108a or an optically transparent needle guide insert 108b. Referring specifically to FIG. 3, the trans-illuminating needle guide device 100 can include features 150 that indicate a plurality of needle insertion depths that correspond to a plurality of grooves. In some embodiments, the features 150 include ruled markings on and a plurality of ridges projecting from an external surface of the housing 102, which indicate a needle insertion depth, as shown in FIG. 3. In some embodiments, the ruled markings may be provided in metric units or English units or provided as a dimensionless scale. In some embodiments, the ruled markings are evenly distanced from one another (e.g., distanced at every 1 mm).

Referring specifically to FIG. 4, the pair of opposing side walls of the needle guide insert 108b (and of needle guide inserts 108 and 108b) define a track 156 configured to receive and engage a projection 154 of the pair of opposing inner walls 158 of the base 104. The projection 154 is an elongated projection that protrudes outwardly from a surface of the pair of opposing inner walls 158. The projection 154 and track 156 extend longitudinally along a length of the side walls of the needle guide insert 108b and are parallel to a bottom surface of the trans-illuminating needle guide device 100. The pair of opposing side walls is parallel to and configured to abut the pair of opposing inner walls 158 of the base 104 when the projection 154 is received and engaged by the track 156.

Disclosed herein, in certain embodiments, are methods of guiding a needle into and illuminating an AV fistula or AV graft or AV graft in a subject. In some embodiments, the AV fistula or AV graft or AV graft may be a superficial AV fistula or AV graft, a superficial AV graft, a deep AV fistula or AV graft, or a deep AV graft. First, once the subcutaneous depth and/or location in an X-Y plane of the patient's anatomy (e.g., a forearm) of a blood vessel (e.g., an AV fistula or AV graft or AV graft) has been established using an ultrasound device (e.g., venous mapping), the user knows the desired needle insertion depth to be selected using the trans-illuminating needle guide device. Next, the methods include inserting the needle guide insert including the needle guide into the base of the housing, if not inserted already. The needle guide insert can be inserted into the base by aligning the projection of the base with the track of the needle guide insert, sliding the needle guide insert along the projection, and push the needle guide insert inward until the pair of deflectable tabs is in the engaged position. The needle guide is inserted into the needle guide insert by compressing the first and second deflectable plates towards each other and aligning and inserting the edges of the plates with the openings of the first and second angled slots, respectively at the proximal ends. The methods can further include placing the trans-illuminating needle guide device, including the needle guide insert, device on a skin surface of the subject and illuminating the skin surface and a subcutaneous tissue of the subject using a plurality of light sources (e.g., LEDs), thereby locating the AV fistula or AV graft or AV graft within the subcutaneous tissue. The methods can further include selecting the desired needle insertion depth by compressing the first and second deflectable plates of the needle guide towards each other such that the protrusion is moved to a disengaged position, sliding the first and second deflectable plates along the first and second angled slots, and releasing the first and second deflectable plates such that the protrusion is engaged with the correct groove corresponding to the desired needle insertion depth. Next, the methods can include inserting the needle into a guide channel of the needle guide to guide the needle, and inserting the needle into the AV fistula or AV graft or AV graft at the selected needle insertion depth. On lifting the device gently, the needle in the AV fistula or AV graft or AV graft disengages from the needle guide and the needle is secured in place (in the AV fistula or AV graft or AV graft) by a practitioner (e.g., a nurse or technician).

While this specification contains many specific implementation details, these should not be construed as limitations on the scope of any method or device or of what may be claimed, but rather as descriptions of features that may be specific to particular embodiments of particular methods and devices. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described herein as acting in certain combinations and even initially claimed as such, one or more features from a claimed combination can in some cases be excised from the combination, and the claimed combination may be directed to a sub-combination or variation of a sub-combination.

Particular embodiments of the subject matter have been described. Other embodiments are within the scope of the following claims. For example, the actions recited in the claims can be performed in a different order and still achieve desirable results.

What is claimed is:

1. A trans-illuminating needle guide device for guiding a needle into and illuminating an arteriovenous (AV) fistula or AV graft in a subject, comprising:
   a housing comprising a base;
   a needle guide insert having a pair of opposing side walls defining a first angled slot, a second angled slot, and a plurality of grooves, the needle guide insert configured to be removably coupled to the base;
   a needle guide having a guide channel configured to receive the needle, a first deflectable plate configured to be received by the first angled slot and the plurality of grooves, and a second deflectable plate configured to be received by the second angled slot;
   a first plurality of light emitting diodes (LEDs) disposed within the housing and configured to emit light of a first wavelength; and
   a second plurality of LEDs disposed within the housing and configured to emit light of a second wavelength, the second wavelength differing from the first wavelength,
   wherein each groove of the plurality of grooves corresponds to a different needle insertion depth, and
   wherein the first and second pluralities of LEDs are configured to illuminate the AV fistula or AV graft or the AV graft of the subject.

2. The trans-illuminating needle guide device of claim 1, wherein the needle guide insert comprises a pair of deflectable tabs, each deflectable tab of the pair of deflectable tabs comprising a hook configured to engage a recess defined by the base.

3. The trans-illuminating needle guide device of claim 2, wherein the guide channel is an open channel having a semi-cylindrical cross-section.

4. The trans-illuminating needle guide device of claim 1, wherein the first deflectable plate comprises a pair of protrusions, each protrusion of the pair of protrusions extending from opposing edges of the first deflectable plate and configured to engage a groove from the plurality of grooves.

5. The trans-illuminating needle guide device of claim 4, wherein each protrusion extends from the opposing edges in a direction that is perpendicular to a surface of the first deflectable plate.

6. The trans-illuminating needle guide device of claim 1, wherein the first and second deflectable plates form a vertex and define an acute angle.

7. The trans-illuminating needle guide device of claim 1, wherein the AV fistula or AV graft or the AV graft is: i) a superficial AV fistula or a superficial AV graft located at subcutaneous depth of less than about 4 millimeters (mm) from a skin surface, or ii) a deep AV fistula or a deep AV graft located at subcutaneous depth of more than about 4 mm from a skin surface.

8. The trans-illuminating needle guide device of claim 1, wherein the pair of opposing side walls define a track configured to engage a projection of a pair of opposing inner walls of the base.

9. The trans-illuminating needle guide device of claim 8, wherein the pair of opposing side walls is parallel to and configured to abut the pair of opposing inner walls when the projection is engaged by the track.

10. The trans-illuminating needle guide device of claim 1, wherein the first and second pluralities of LEDs are arranged in a U-shape.

11. The trans-illuminating needle guide device of claim 1, wherein the first wavelength ranges from about 620 nanometers (nm) to about 700 nm.

12. The trans-illuminating needle guide device of claim 1, wherein the second wavelength ranges from about 600 nm to about 615 nm.

13. The trans-illuminating needle guide device of claim 1, wherein the LEDs are configured to emit light at an angle of dispersion of about 25 degrees.

14. The trans-illuminating needle guide device of claim 1, wherein the needle insertion depth ranges from about 1 mm to about 8 mm.

15. The trans-illuminating needle guide device of claim 1, wherein the needle guide insert is optically transparent or opaque.

16. The trans-illuminating needle guide device of claim 1, wherein the angle of the needle is about 30 degrees to about 39 degrees.

17. The trans-illuminating needle guide device of claim 11, wherein the projection and track extend longitudinally and are parallel to a bottom surface of the base.

* * * * *